(12) United States Patent
Pena et al.

(10) Patent No.: US 6,495,157 B1
(45) Date of Patent: Dec. 17, 2002

(54) INTRAVAGINAL CLINDAMYCIN OVULE COMPOSITION

(75) Inventors: Lorraine Elisabeth Pena; Phil Bryan Bowman, both of Kalamazoo; Robert Shih-Liang Chao, Portage; Carolyn V. Pesheck, Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/619,930

(22) Filed: Jul. 20, 2000

Related U.S. Application Data

(60) Provisional application No. 60/147,561, filed on Aug. 6, 1999.

(51) Int. Cl.[7] .............................. A61F 6/06; A61F 6/08; A61F 6/00; A61K 9/14; A61K 9/02

(52) U.S. Cl. ........................ 424/433; 424/430; 424/422; 424/489; 424/502

(58) Field of Search .................................. 424/430, 433, 424/489, 502

(56) References Cited

FOREIGN PATENT DOCUMENTS

WO          WO-97/44032 A1 * 11/1997

* cited by examiner

Primary Examiner—Thurman K. Page
Assistant Examiner—Rachel M. Bennett
(74) Attorney, Agent, or Firm—Bruce A. Pokras; Karen B. King

(57) ABSTRACT

A highly storage-stable composition for vaginal administration of clindamycin is disclosed which is useful for the treatment of bacterial vaginosis. The composition is a vaginal suppository containing an antimicrobially effective amount of clindamycin dispersed in a Hard Fat NF suppository base. Hard Fat NF suppository bases provide a clindamycin product having long term storage stability while providing efficacy against bacterial vaginosis which is equivalent to clindamycin vaginal creams.

11 Claims, 2 Drawing Sheets

X-ray Diffraction Patterns Showing the Various Crystal Forms of a Suppository during the Polymorphic Transition. The Peaks at 15-25° 2θ Represent the Peaks Associated with the Polymorphic Transition of the Base.

A. α

B. α'

C. β

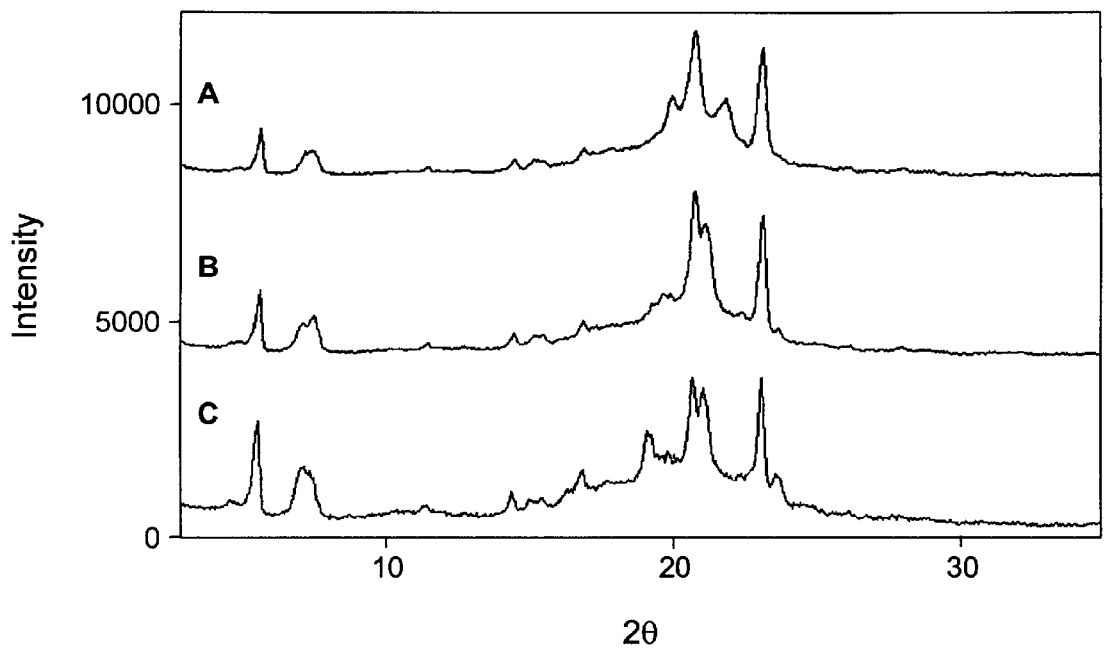
Figure 1. X-ray Diffraction Patterns Showing the Various Crystal Forms of a Suppository during the Polymorphic Transition. The Peaks at 15-25° 2θ Represent the Peaks Associated with the Polymorphic Transition of the Base.
A. α
B. α'
C. β

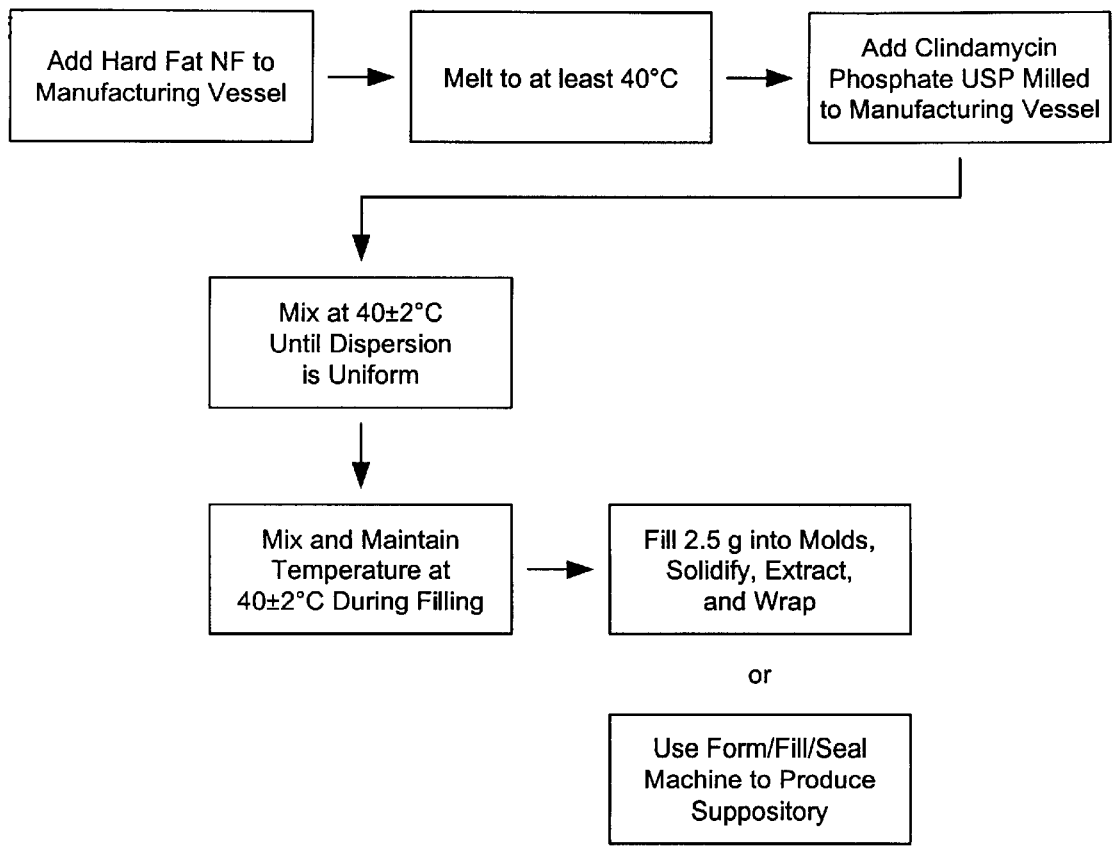
Figure 2. Manufacturing Flow Chart for Clindamycin Vaginal Suppositories.

INTRAVAGINAL CLINDAMYCIN OVULE COMPOSITION

CROSS REFERENCE TO RELATED APPLICATIONS

The present patent application claims the benefit of the following provisional application: U.S. Serial No. 60/147,561, filed Aug. 6, 1999, under 35 USC 119(e)(i).

BACKGROUND OF THE INVENTION

The present invention is directed to a treatment for bacterial vaginosis (BV). The exact etiology of BV is unclear although it appears to result from an overgrowth of organisms in the vaginal flora. Although generally a mild condition, BV is distressing to the patient because of the unpleasant vaginal odor and discharge. In addition, it is epidemiologically linked to several urogenital diseases. Clindamycin vaginal cream (CVC) 100 mg per day for 7 days is a standard treatment for BV. It has recently been demonstrated that a 3-day treatment course of CVC is as effective as a 7-day course. However, even with a 3-day treatment, the use of creams is considered to be inconvenient. A vaginal ovule (suppository) formulation containing clindamycin would offer patients an alternative, more convenient dosage form. Therefore, the development of a vaginal suppository having at least the same efficacy as CVC was undertaken. As a result of this development effort, it was discovered that Hard Fat NF suppository bases significantly increased the storage stability of clindamycin.

SUMMARY OF THE INVENTION

We have developed a highly storage-stable composition for vaginal administration of clindamycin which comprises a vaginal suppository containing an antimicrobially effective amount of clindamycin dispersed in a Hard Fat suppository base, preferably Hard Hat NF grade. Hard Fat bases are a mixture of glyceride esters of higher saturated fatty acids. The Hard Fat NF suppository bases provide a clindamycin product having increased stability over the CVC formulation while providing equivalent efficacy against BV.

BRIEF DESCRIPTION OF THE DRAWINGS

FIG. 1 shows an x-ray diffraction pattern of the different polymorphic transitions that a Hard Fat NF suppository base containing clindamycin will go through over time.

FIG. 2 is a schematic of a system for preparing suppositories of the present invention.

DETAILED DESCRIPTION OF THE INVENTION

The present invention comprises a composition for intravaginal administration of clindamycin which composition contains an antimicrobially effective amount of clindamycin dispersed in a Hard Fat NF base. Hard Fat is defined in the National Formulary as "a mixture of glycerides of saturated fatty acids." It was surprisingly found that clindamycin is extremely storage stable in a Hard Fat NF base.

Clindamycin is an antibiotic also known as methyl 7-chloro-6,7,8-trideoxy-6-(1-methyl-trans-4-propyl-L-2-pyrrolidinecarboxamido)-1-thio-L-threo-α-D-galacto-octo-pyranoside or methyl 7-chloro-6,7,8-trideoxy-6-[[(1-methyl-4-propyl-2-pyrrolidinyl)carbonyl]amino]-1-thio-L-threo-α-D-galacto-octo-pyranoside. As used herein the term "clindamycin" alone includes free-base clindamycin as well as the pharmaceutically acceptable salts and esters thereof. Examples of clindamycin pharmaceutically acceptable salts and esters are clindamycin hydrochloride, clindamycin phosphate, clindamycin palmitate and clindamycin palmitate hydrochloride. It is preferred to use a clindamycin salt or ester in the composition of the invention, with clindamycin phosphate being especially preferred.

The uses, properties and methods of synthesis of clindamycin are set forth in U.S. Pat. No. 3,969,516, Stoughton, issued Jul. 13, 1976; U.S. Pat. No. 3,475,407, Bierkenmeyer, issued in 1969; U.S. Pat. No. 3,487,068, issued in 1969; U.S. Pat. Nos. 3,509,127 and 3,544,551, Kagan and Magerlein, issued in 1970; U.S. Pat. No. 3,513,155, Bierkenmeyer and Kagan, issued in 1970; Morozowich and Sinkula, U.S. Pat. No. 3,580,904 issued in 1971 and U.S. Pat. No. 3,655,885 issued in 1972; U.S. Pat. No. 3,714,141, issued in 1973; U.S. Pat. No. 4,568,741 issued in 1986; U.S. Pat. No. 4,710,565, issued in 1984; (all of the foregoing patents being incorporated herein by reference).

Additional knowledge in the art concerning clindamycin is found in Magerlein, et al, Antimicro. Ag. Chemother. (1966) 727; Birkenmeyer and Kagan, J. Med. Chem., 13, 616 (1970); Oesterling, J. Pharm Sci. 59, 63 (1970); McGehee, et al, Am. J. Med. Sci. 256, 279 (1968); D. A. Leigh, J. Antimicrob. Chemother. 7 (Supplement A), 3 (1981); J E Gray et al. Toxicol. Appl. Pharmacol. 21, 516 (1972) and L W Brown and W F Beyer in Analytical Profiles of Drug Substances, Vol 10, K. Florey, editor (Academic Press, New York, 1981) pages 75–91.

The compositions of the present invention must be solid at room temperature, and preferably have a flow point in the range of 30–40° C.; more preferably 30–37° C. The flow point is visually determined based upon heating a sample from 25° C. at a rate of 2° C./minute and observing the temperature at which rapid flow of the sample occurs. This measurement is conveniently carried out using a microscope equipped with a video camera having on-screen digital monitoring of the temperature.

Hard Fat NF suppository bases undergo a polymorphic transition during storage. The stages of the transition are designated α, α' and β, with the β form being the final, most stable polymorph. Thus, the flow point of a composition immediately after manufacture will increase slowly until the transition is complete. Using conventional x-ray diffraction techniques, the polymorphic transition from the α to β forms may be monitored from the time of the initial suppository manufacture until no further changes in the diffraction pattern over a period of time are evident. An example of the α, α' and β x-ray diffraction patterns is shown in FIG. 1. The flow points described above refer to the flow point following completion of the polymorphic transition.

The composition of the present invention contains an antimicrobially effective amount of clindamycin for the treatment of BV. Preferably, the composition contains 10–800 mg of clindamycin, or its salts or ester expressed as the free base. More preferably, the composition of the invention contains 25–300 mg, especially 50–200 mg, and most preferably 50–150 mg.

The total weight of a composition of the invention will vary according to the amount of active ingredient and "ease of use" characteristics such as size and shape of the resulting suppository, and is therefore not critical. Generally, lower amounts of active ingredient may be accommodated by a smaller size suppository, and higher amounts of active ingredient will require a larger size suppository. Manufacturing properties, such as the viscosity of the clindamycin base dispersion when the base is in the molten state during processing, will also determine the minimum amount of suppository base that is needed to disperse, mold and package a suppository having a given amount of clindamycin. Such a parameter is not critical to the present invention, and may be determined in the course of routine optimization of the manufacturing process. Typical suppositories would be in the range of 0.5 to 10 g, preferably 1 to 5 g, and most preferably 2 to 3 g. Thus, compositions would generally be in the range of 0.1% to 60% clindamycin. Preferably 0.5% to 30%, more preferably 1.5% to 10%, and most preferably 1.5% to 7.5%.

The suppository bases useful in accordance with the present invention are any pharmaceutically acceptable Hard Fat NF bases. Useful Hard Fat NF suppository bases are manufactured by Condea Vista Company, Cranford, N.J. under the WITEPSOL® trademark, and by Stepan Company, Northfield, Ill. under the WECOBEE® trademark. Further useful suppository bases are those manufactured by Gattefosse Etablissements, Saint Priest, France under the SUPPOCIRE® trademark. The WITEPSOLs are described by their manufacturer as being "glyceride esters of saturated $C_{12}$–$C_{18}$ fatty acids." The WECOBEEs are described by their manufacturer as being "a triglyceride derived from vegetable oil." The SUPPOCIREs are described by the manufacturer as hydrogenated palm kernel glycerides and hydrogenated palm glycerides.

The preferred Hard Fat NF suppository bases are a mixture of glyceride esters of vegetable $C_{12}$–$C_{18}$ saturated fatty acids. The majority of the glyceride esters are preferably triglycerides. The vegetable source is preferably coconut and palm kernel oils. The most preferred Hard Fat NF base is a mixture of triglyceride esters of coconut and palm kernel oil $C_{12}$–$C_{18}$ saturated fatty acids having the following characteristics in the absence of clindamycin:

Open-tube melting point: 31.0–33.0° C. (α polymorphic form)
Solidification point: 30.0–32.5° C. (α polymorphic form)
Hydroxyl value max. 3 mg potassium hydroxide/g
Saponification value: 240–250 mg potassium hydroxide/g
Diglycerides max. 15% by weight
Monoglycerides max 1% by weight All the above tests should be performed in accordance with standardized procedures, e.g., United States Pharamacopoeia or European Pharamacopoeia.

The bases for use in accordance with the invention may be produced by any conventional means. One means is the blending $C_{12}$–$C_{18}$ saturated fatty acids, preferably derived from coconut and palm kernel oils, followed by esterifying the mixture with glycerol. Routine variations in the blend of saturated fatty acids and in the esterification conditions will enable the production suppository bases having the desired properties. A commercially available base which meets the "most preferred" specification, above, is WITEPSOL® H-32 (Condea Vista Company, Cranford, N.J.). A typical composition of the suppository using WITEPSOL® H-32 is presented in Table 1.

TABLE 1

Composition of Clindamycin Phosphate Vaginal Suppository

| Amount per Suppository | Component |
| --- | --- |
| 100 mg[1] | Clindamycin phosphate USP (milled) |
| 2375 mg | Witepsol H-32 (Hard Fat NF) |

[1]expressed in terms of the clindamycin free base. Actual amount of clindamycin phosphate used is calculated on the basis of potency assay (e.g., USP).

Hard Fat NF suppository bases provide a high level of storage stability to clindamycin. Assays carried out after as much as sixty months of storage at room temperature show that virtually no clindamycin degradation has occurred in the suppositories of the invention.

The suppositories of the present invention may also contain additives, such as stabilizers (e.g., antioxidants and other types of preservatives), polymorphic transition accelerators (e.g., tristearin), biocompatible polymers, surfactants, dispersants, water absorbents and the like. The use of biocompatible polymers, surfactants and water absorbents are described in U.S. Pat. No. 4,765,978, the disclosure of which is hereby incorporated by reference. The concentration of these additives may vary according to the particular additive used and the desired result sought. The use of the kind and concentration of additives are well within the ability of the skilled artisan.

When clindamycin is used in the manufacture of the suppository of the invention, the drug particles preferably have a volume median diameter ("particle size") of not more than 10 μm. The minimum particle size is not critical, but should not be so small as to cause problems in the manufacture of the suppositories. Particle sizes as low as 0.5 μm would be satisfactory. The use of reduced particle size drug versus the unmilled drug in the suppository reduces vaginal irritation in the ovariectomized rat model even when a water soluble salt or ester of clindamycin, such as the phosphate ester, is used. Such a reduction of irritation is surprising given the fact that water soluble salts and esters of clindamycin would be expected to be solubilized in the vaginal fluids too quickly for the larger particles to cause irritation. Therefore, a vaginal suppository containing clindamycin having a particle size of 10 μm or less as described above is another aspect of the invention.

If the particle size of the bulk drug is greater than 10 μm, it may be reduced in particle size by any conventional means, but is preferably milled using a pulverizing rotary mill or air jet micronizer. With the exception of particle size, the physical and chemical characteristics of the milled drug are the same as the unmilled drug.

The vaginal suppository of the present invention may be administered at a dosage and for a duration sufficient to treat the BV of the patient. Preferably, treatment is carried out for one to fourteen days by the administration of one suppository containing 10–800 mg of clindamycin per day, with the dosage at the lower end of the range being administered for the time periods at the higher end of the range, and vice versa. More preferably, treatment is carried out by administration of one suppository containing 50–150 mg, especially about 100 mg, of clindamycin per day for three to seven consecutive days.

The suppositories of the invention may be prepared by any conventional means, such as by hand casting or through the use of an automated "form-fill-seal" suppository machine. In general terms, suppository manufacture may be performed by melting the base to an appropriate selected temperature, incorporating the drug while mixing, and mixing to uniformity. If desired, the molten base may be filtered prior to drug addition, and the drug/base mixture may be homogenized prior to filling. The molten dispersion is maintained at the above selected temperature for filling. If hand filled, the molten base is volumetrically filled into casting molds and allowed to solidify at room temperature. The finished suppositories may then be individually packaged into preformed foil pouches or wrapped. Alternatively, the suppository manufacture may be automated using a form-fill-seal machine. By this method, an open foil shell is formed by the machine and the molten suppository base is volumetrically filled into the shell. The foil is then sealed and the filled shell is transferred to a cooling table or other similar device for solidification. A schematic for preparation of suppositories of the present invention is shown in FIG. 2.

In accordance with all the above, the preferred embodiment of the invention is a vaginal suppository comprising clindamycin having a particle size of 10 μm or less dispersed in a Hard Fat NF suppository base. The suppository is solid at room temperature, and has a flow point of 37° C. or less after reaching the β polymorphic form. In the more preferred embodiment, the Hard Fat NF is a mixture of glyceride esters of vegetable $C_{12}$–$C_{18}$ saturated fatty acids, the majority of which are triglycerides. In the most preferred embodiment, the Hard Fat NF meets the specifications described previously above.

DEFINITIONS

Hard Fat refers to a mixture of triglycerides, diglycerides and monoglycerides, which may be obtained either by esterification of fatty acids of natural origin with glycerol or by transesterification of natural fats. Each type of hard fat is characterised by its melting point, its hydroxyl value and it saponification value.

EXAMPLES

Example 1

Suppository Preparation

A batch of 11,200 suppositories was produced using the following procedure:
1. 29 kg of WITEPSOL H-32 Hard Fat NF base was melted in a manufacturing kettle by heating to 40±2° C. The temperature of the molten suppository base was maintained at 40±2° C. throughout this manufacturing procedure.
2. Using a preheated filter, 26.614 kg of the molten base was transferred to a second manufacturing vessel equipped with a homogenizing mixer.
3. 1.386 kg of clindamycin phosphate equivalent to 1.12 kg of clindamycin free base was added to the kettle and mixed and homogenized to obtain a uniform dispersion.
4. The drug dispersion was transferred to a jacketed kettle and transported to the form/fill/seal suppository machine.
5. While maintaining mixing and a temperature of 40±2° C., the drug dispersion was formed into 2.5 g suppositories using the automated form/fill/seal machine.

Example 2

X-ray Diffraction Examination

The polymorphic transition state of the suppository was determined using a Siemans D-5000 x-ray diffractometer. A sufficient amount of material to fill the diffractometer sample tray was scraped from the suppository and then carefully packed into the tray to ensure a flat surface. The instrument was operated with copper K-$L_3$ radiation at a wavelength of 1.5406 Å with a nickel filter. The instrument parameters were as follows: 45 KV voltage, 40 mA current, 0.2 mm detector aperture. The sample was scanned over the spectral range of 3–40° 2θ at a scan rate of 2° 2θ/min. FIG. 1 shows typical diffraction patterns as the sample goes through the phase transitions from α to α' to β polymorphs.

Example 3

Flow Point Determination

The flow point of a suppository was determined in the following manner: A polarizing microscope with a 20×pol long working distance objective was used in conjunction with a Mettler FP 82 hot stage. A razor blade was used to obtain a small portion of the suppository which was placed on a pre-cleaned slide and covered with a cover slip. Gentle pressure was applied to the cover slip to cause the sample to spread to uniformity, and the slide was placed in the furnace of the hot stage. The sample was heated over the range of 25–40° C. at a rate of 2° C./minute. A video camera was used to observe the heating which was recorded with simultaneous on-screen digital display of the temperature. The flow point was defined as the temperature at which rapid flow of the sample occurred.

Example 4

Effectiveness of Suppository for Treating BV

Three studies utilizing a modified Amsel's criteria (amine odor and clue cells only) were performed. A prospective, randomized, double-blind, multicenter study involving 581 subjects, found CVC 3-day treatment to be as effective as CVC 7-day. Cure rates were 90.1% in the 3-day group and 92.8% in the 7-day (p=0.23) at the post-treatment visit.

A prospective, randomized, observer-blind, multicenter study comparing CVO 3-day to CVC 7-day, involving 662 subjects, found comparable cure rates (81.3%, 72.6%; p=0.02) at the post-treatment visit.

In a prospective, randomized, double-blind, multicenter study involving 399 subjects, CVO 3-day was compared to metronidazole (MET), 7-days. The CVO group had a cure rate of 86.7% at the post-treatment visit as compared to 85.7% in the MET group (p=0.97).

In each of the above studies, a long term follow-up visit showed equivalent cure rates between comparators, although somewhat lower overall. Cure rates for the three studies using Amsel's criteria showed similar patterns of efficacy between the comparators. MET caused 6% more drug-related adverse events than CVO. No clinically significant safety differences were found between CVO and CVC. Adverse events related to the urogenital system were most commonly reported in all treatment groups. The adverse events judged to be associated with treatment did not present substantial risk to the subjects studied and would not be likely to deter clinical usage. The shortened 3-day treatment, whether ovule or cream, demonstrated equivalent efficacy as standard 7-day treatments and may be better tolerated than metronidazole.

What is claimed is:

1. A suppository composition for vaginal administration of clindamycin which composition comprises an antimicrobially effective amount of clindamycin, or a pharmaceutically acceptable salt or ester thereof, in the form of drug particles dispersed in a Hard Fat suppository base, wherein the drug particles have a volume median diameter of about 0.5 $\mu$m to about 10 $\mu$m.

2. The composition of claim 1 wherein the composition contains 10 to 800 mg of clindamycin, or its salt or ester expressed as the free base, whereby said clindamycin, or its salt or ester, is present in said composition in an amount from about 0.1% by weight of the entire composition to about 60% by weight of the entire composition.

3. The composition of claim 2 wherein the composition has a flow point in the range from 30° C. to 40° C.

4. The composition of claim 3 wherein said composition contains 25 to 300 mg of clindamycin, or its salt or ester expressed as the free base, wherein said clindamycin, or its salt or ester, is present in said composition in an amount from about 0.5 % by weight of the entire composition to about 30% by weight of the entire composition.

5. The composition of claim 4 wherein said Hard Fat has a $\beta$ polymorphic form which has a flow point of 37° C. or less.

6. The composition of claim 5 wherein the Hard Fat is a mixture of glyceride esters of vegetable $C_{12}$–$C_{18}$ saturated fatty acids containing more than 50% triglyceride esters.

7. The composition of claim 6 wherein said composition contains 50 to 200 mg of clindamycin, or its salt or ester expressed as the free base, wherein said clindamycin, or its salt or ester, is present in said composition in an amount from about 1.5% by weight of the entire composition to about 10% by weight of the entire composition.

8. The composition of claim 7 wherein the clindamycin is a clindamycin salt or ester.

9. The composition of claim 6 wherein said composition contains 50 to 150 mg of the clindamycin salt or ester expressed as the free base and is present in said composition in an amount from about 1.5% by weight of the entire composition to about 7.5% by weight of the entire composition.

10. The composition of claim 9 wherein the clindamycin is clindamycin phosphate.

11. The composition of claim 1 wherein the Hard Fat is Hard Fat NF grade which has the following additional properties:

Open-tube melting point: 31.0–33.0° C. ($\alpha$ polymorphic form)
Solidification point: 30.0–32.5° C. ($\alpha$ polymorphic form)
Hydroxyl value max. 3 mg potassium hydroxide/g
Saponification value: 240–250 mg potassium hydroxide/g
Diglycerides max. 15% by weight
Monoglycerides max 1% by weight.

* * * * *